United States Patent
MacLauchlan et al.

(10) Patent No.: US 6,192,760 B1
(45) Date of Patent: Feb. 27, 2001

(54) EMAT TRANSMIT/RECEIVE SWITCH

(75) Inventors: Daniel T. MacLauchlan, Lynchburg; Charles B. Overby, Campbell County, both of VA (US)

(73) Assignee: McDermott Technology, Inc., New Orleans, LA (US)

( * ) Notice: Subject to any disclaimer, the term of this patent is extended or adjusted under 35 U.S.C. 154(b) by 0 days.

(21) Appl. No.: 09/377,453

(22) Filed: Aug. 19, 1999

(51) Int. Cl.$^7$ ................................. G01N 29/04; H02J 3/06

(52) U.S. Cl. ................................................................ 73/643

(58) Field of Search ........................... 73/643, 599, 597, 73/598, 600, 620, 627, 629

(56) References Cited

U.S. PATENT DOCUMENTS

| | | |
|---|---|---|
| 2,277,037 | 3/1942 | Clark et al. . |
| 3,357,556 | 12/1967 | Martner et al. . |
| 3,553,636 | 1/1971 | Baird . |

(List continued on next page.)

FOREIGN PATENT DOCUMENTS

| | | |
|---|---|---|
| 56-21058 | 2/1981 | (JP) . |
| 57-165761 | 10/1982 | (JP) . |
| 58-92825 | 6/1983 | (JP) . |

OTHER PUBLICATIONS

P. J. Latimer et al., "Improved EMAT Probe for Weld Inspections," RDD:94:31002:0050–01:01, Jun. 24, 1993, 19 page Technical Report, Babcock & Wilcox Co., Lynchburg, Virgina.

P. J. Latimer et al., "EMAT Inspection of 2219 Aluminum and Aluminum/Lithium Alloy Welds," RDD:93:30001–009–001:01, Jan. 1993, 14 page Technical Report, Babcock & Wilcox, Lynchburg, Virgina.

B. W. Maxfield et al., "Evaluating EMAT Designs for Selected Applications," *Materials Evaluation*, Oct. 1987, pp. 1166–1183, vol. 45.

(List continued on next page.)

*Primary Examiner*—Hezron Williams
*Assistant Examiner*—Rose Miller
(74) *Attorney, Agent, or Firm*—R. J. Edwards; Eric Marich; R. C. Baraona

(57) ABSTRACT

A transmitting and receiving switch assembly for an electromagnetic acoustic transducer (EMAT) and a method for selectively switching an EMAT between transmit mode and receive mode both use a particular circuit. This circuit contains an EMAT coil coupled to a tuning capacitor, which allows the EMAT to be operated at a desired frequency when transmitting. A set of capacitors separates the EMAT coil from a set of diode strings (preferably containing at least one fast switching silicon diode), which are joined by a resistive connection. A transformer, which is center tapped at its primary winding, is coupled to the other end of the diode strings. Finally, a receiver input is connected to the transformer. In operation, the frequency of the EMAT is set by appropriately energizing and tuning the tuning capacitor. A voltage is then applied in the center tapped transformer and in the resistive link between the diode strings. The current automatically switches the conductivity of the diodes and permits the EMAT to switch modes as desired. Likewise, the method disclosed also utilizes this circuit, as described above, and involves several steps. First, the EMAT frequency must be selected and set, using the tuning capacitor. Then, a voltage is applied within the circuit to induce transmission by the EMAT. Next a sinusodial toneburst is given within the circuit to switch the transmit/receive capabilities of the EMAT, and then observing the input received by the EMAT-thereby permitting the alternate switching of the EMAT from receive to transmit mode in a matter of nanoseconds.

13 Claims, 2 Drawing Sheets

U.S. PATENT DOCUMENTS

| | | |
|---|---|---|
| 3,802,252 | 4/1974 | Hayward et al. . |
| 3,832,885 | 9/1974 | Hayward et al. . |
| 3,868,847 | 3/1975 | Gunkel . |
| 3,913,383 | 10/1975 | Kreula et al. . |
| 4,100,809 | 7/1978 | Bobrov et al. . |
| 4,144,766 | 3/1979 | Wehrmeister . |
| 4,149,421 | 4/1979 | Bottcher et al. . |
| 4,208,915 | 6/1980 | Edwards . |
| 4,289,030 | 9/1981 | Alers et al. . |
| 4,296,486 | 10/1981 | Vasile . |
| 4,384,476 | 5/1983 | Black et al. . |
| 4,481,824 | 11/1984 | Fujimoto et al. . |
| 4,580,448 | 4/1986 | Skrgatic . |
| 4,593,568 | 6/1986 | Telford et al. . |
| 4,596,147 | 6/1986 | Behl et al. . |
| 4,637,065 | 1/1987 | Ruppel ................................ 455/78 |
| 4,710,710 | 12/1987 | Flora et al. . |
| 4,821,573 | 4/1989 | Nagata et al. . |
| 4,848,924 | 7/1989 | Nuspl et al. . |
| 4,856,337 | 8/1989 | Metala et al. . |
| 5,050,703 | 9/1991 | Graff et al. . |
| 5,060,518 | 10/1991 | Aleshin et al. . |
| 5,085,082 | 2/1992 | Cantor et al. . |
| 5,140,860 | 8/1992 | Huschelrath et al. . |
| 5,154,081 | 10/1992 | Thompson et al. . |
| 5,164,921 | 11/1992 | Graff et al. . |
| 5,237,874 | 8/1993 | Latimer et al. . |
| 5,343,785 | 9/1994 | Holt et al. . |
| 5,359,898 | 11/1994 | Latimer . |
| 5,372,042 | 12/1994 | Jarman et al. . |
| 5,396,800 | 3/1995 | Drinon et al. . |
| 5,436,873 | 7/1995 | MacLauchlan et al. . |
| 5,439,157 | 8/1995 | Geier et al. . |
| 5,449,958 * | 9/1995 | MacLauchlan et al. ................ 307/17 |
| 5,497,662 | 3/1996 | Dykes . |
| 5,511,424 * | 4/1996 | MacLauchlan et al. ................ 73/609 |
| 5,537,876 | 7/1996 | Davidson et al. . |
| 5,608,164 | 3/1997 | MacLauchlan . |
| 5,675,087 | 10/1997 | MacLauchlan et al. . |
| 5,708,354 | 1/1998 | Hancock et al. . |
| 5,760,307 | 6/1998 | Latimer et al. . |
| 5,837,898 | 11/1998 | MacLauchlan . |
| 5,866,820 | 2/1999 | Camplin et al. . |

OTHER PUBLICATIONS

R. B. Thompson et al., "An Elastic–wave Ellipsometer for Measurement of Material Property Variations," *Appl. Phys. Lett.*, Jan. 15, 1979, pp. 128–130, vol. 34, No. 2.

Article entitled "EMATs –Ultrasonic Inspection without Couplant," 2 pages, published by The Babcock & Wilcox Company, Lynchburg, Virginia.

B. W. Maxfield et al., "The Design and Use of Electromagnetic Acoustic Wave Transducers (EMATs)," *Materials Evaluation*, Nov. 1983, pp. 1399–1408, vol. 41, published by American Society for Nondestructive Testing, Inc.

Vicor Express Catalog, 1995, pp. 24–25, printed in U.S. by W. E. Andrews.

* cited by examiner

EMAT TRANSMIT/RECEIVE SWITCH

FIELD AND BACKGROUND OF THE INVENTION

Transmit/Receive (T/R) switches are used extensively in radio communications electronics. In these applications, the T/R switch is used to couple an antenna to the transmitter and receiver electronics in a manner such that when transmitting, the majority of the transmitter power goes to the antenna and when receiving, the majority of the signal received by the antenna goes to the receiver. The T/R switch also protects the receiver circuitry from being damaged by large transmitter signals through limiting the power that gets to the receiver input section. Several different kinds of electronic circuits have been employed to perform the T/R switch function.

U.S. Pat. No. 4,637,065 to Ruppel discloses one type of T/R switch used in radio communications circuits and contains a good description of the prior art. These types of T/R switch circuits utilize PIN diodes, giving rise to a long switch over time of several milliseconds, which is adequate for most radio communications applications. However, a T/R switch suitable for use with Electromagnetic Acoustic Transducers (EMATs) must be very fast acting; that is, capable of switching from transmit mode to receive mode in a few microseconds or less. Thus, a drawback to using these type of T/R switches for EMAT operation is that the time it takes for the circuit to recover from the transmit mode and then switch to the receive mode is too long.

Another method of coupling the transmitter and receiver to the same transducer is to attach the output of the transmitter directly to the transducer and attach the input to the receiver to the transducer via resistors. As illustrated in FIG. 1, a back-to-back diode (CR11 and CR12) arrangement is placed at the input to the receiver to prevent damage to the receiver circuit from the large transmitter voltages with the current being limited by the resistors. This allows rapid switching from transmit mode to receive mode. However, the use of resistors to couple the transducer to the receiver input results in transmit power loss in the resistors and signal to noise reduction from the receiver because of the increased resistance at the receiver input, so that this arrangement is not well-suited for use with EMATs.

FIG. 2 illustrates another T/R switch circuit known to the inventor prior to the current invention. In this T/R switch, the transmitter output is coupled directly to the transducer. The transducer is then coupled to the receiver input via a power limiting circuit formed by diodes CR1 and CR2, inductor L1, resistor R1, voltage source V1, and transformer T1. Direct current (D.C.), supplied from V1 and limited by resistor R1, flows through the diodes CR1 and CR2. This D.C. is set by R1 such that the diodes are biased "on" for small signals; that is, a small received signal passes from the transducer to the receiver input unimpeded because the diodes are put into a conductive state (low resistance) by the D.C. bias currents. Inductor L1 provides a high impedance for the radio frequency (RF) signals preventing them from flowing through voltage source V1. High voltage RF signals applied to the transducer cause the diodes to become reverse biased, switching them into a nonconductive state. This switching time depends on what diodes are employed in the circuit.

In the circuit illustrated in FIG. 2, the diodes employed had switching times on the order of $1/10$ of a microsecond. However, the $1/10$ of a microsecond switching time limited the operation to frequencies below approximately 2 MHz because the diodes must switch on and off with each cycle of the transmitter RF toneburst. Consequently, one disadvantage to using this circuit for EMAT operation is that it is single ended (one side of the transducer is connected to ground), and those skilled in the art have found that, in order to prevent noise pickup, the EMAT coil is best kept isolated from ground and operated into a differential input receiver which provide high common mode noise rejection. Likewise, the D.C. bias current flowing through the primary windings of T1 can cause the transformer core to saturate if it is not of adequate size resulting in larger transformer size than would otherwise be necessary. Therefore, the circuit illustrated in FIG. 2 is not well-suited for use with EMATs.

In sum, it is apparent that an improved T/R switch suitable for use with an EMAT is needed to overcome the deficiencies discussed above. Moreover, such an improved T/R switch for use with an EMAT would be welcome by the industry.

SUMMARY OF THE INVENTION

The present invention seeks to improve the T/R switching capabilities during EMAT operation. Specifically, the T/R switch disclosed in the present invention provides several advantages for EMAT operation. This circuit blocks the transmitter pulses from being sent to the input to the receiver, while allowing the small received signals to be applied to the input to the receiver with very little attenuation or added source resistance. Additionally, since this circuit is balanced with respect to ground, good common mode noise rejection is obtained.

Assuming that the input impedance is infinite, the use of resistors to couple the received signal from the EMAT to the input to the receiver reduces the signal to noise ratio by a factor of two, as compared to an ideal T/R switch. That is, in prior art circuits, the input impedance of the receiver may actually be low enough, especially at high frequencies, to produce significant attenuation of the received signals if resistors are placed between the transducer and the receiver input. In lab testing of the present invention, an improvement in signal to noise of a factor of three was observed when this T/R switch was substituted for resistor coupling between the transducer and the EMAT receiver during operation at 5 MHz. In many applications, these improvements in signal to noise ratio can mean the difference between being able to perform the test and not being able to perform the test.

Also, receiver input transformer core saturation is prevented in the present invention by using a center tapped primary with the bias current flowing in opposite directions in each half of the primary windings. This use of a center tapped primary allows very small receiver input transformers to be constructed.

One aspect of the present invention is drawn to an improved electrical circuit which utilizes an EMAT as both a transmitter and a receiver by allowing the fast switching of the EMAT from transmit to receive mode, and vice versa. In addition to an EMAT coil, this circuit contains a tuning capacitor which allows the EMAT to be operated at a desired frequency when transmitting. The EMAT is also coupled to a pair of capacitors which are, in turn, connected to two separate diode strings. The diode strings preferably contain at least one fast switching silicon diode, although the use of similar diodes is possible. The diode strings are also resistively connected to each other at their respective junctions with the capacitors. The other end of each diode string is coupled to a single transformer, which is center tapped at its primary winding. Finally, the transformer is coupled to an input receiver.

In operation, the frequency of the EMAT is set by appropriately energizing and tuning the tuning capacitor. A voltage is then applied in the center tapped transformer and in the resistive link between the diode strings. The current automatically switches the conductivity of the diodes and permits the EMAT to switch modes as desired.

Another aspect of the present invention is drawn to an improved method for selectively switching an EMAT between transmitting mode and receiving mode. Essentially, this method utilizes a circuit, as described above, and involves several steps. A sinusodial toneburst voltage is applied across the terminals of the EMAT coil to induce transmission by the EMAT. The large applied voltages reverse bias the diode strings, effectively switching off the input to the receiver section. When the transmitter voltage is turned off, the diodes are biased on by the current supplied by D.C. power source through current limiting resistors, effectively turning on the input to the receiver section.

The various features of novelty which characterize the invention are pointed out with particularity in the claims annexed to and forming a part of this disclosure. For a better understanding of the invention, its operating advantages, and the specific objects attained by its uses, reference is made to the accompanying drawings and descriptive matter in which the preferred embodiments of the invention are illustrated.

DESCRIPTION OF THE PREFERRED EMBODIMENTS

Figure 1:
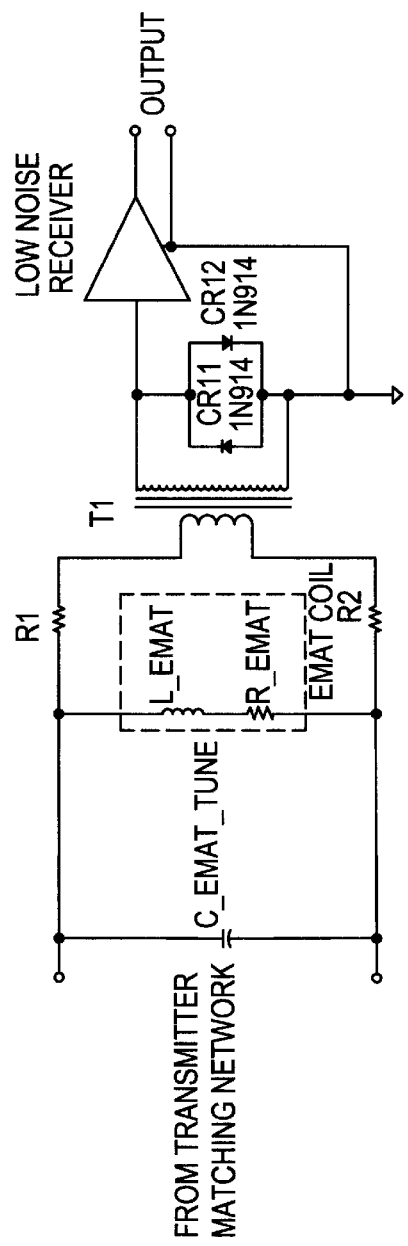
FIG. 1 is a schematic representation of a first known T/R switch.
Figure 2:
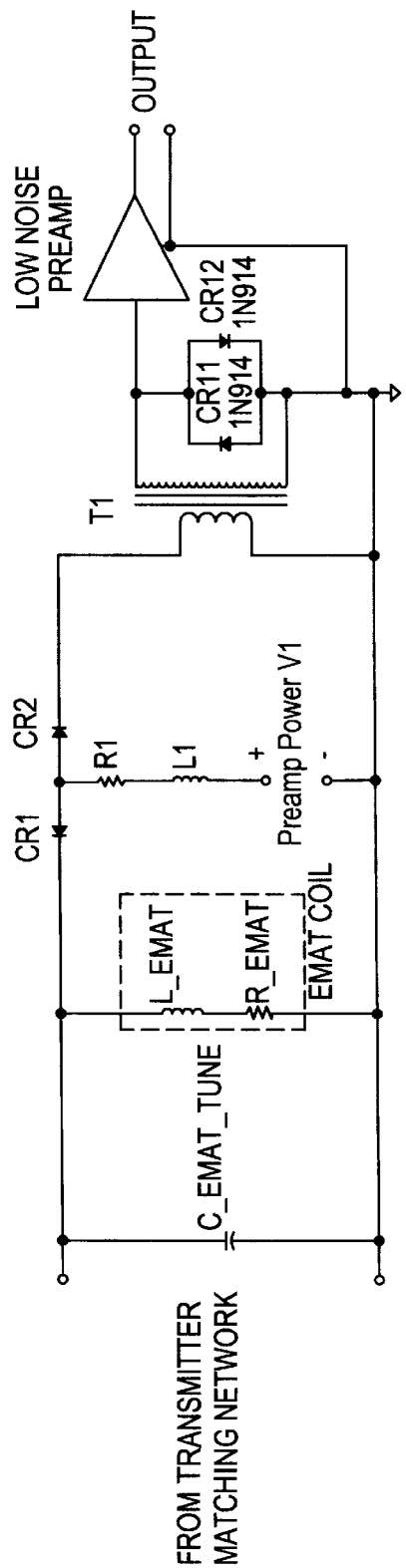
FIG. 2 is a schematic representation of a second known T/R switch.
Figure 3:
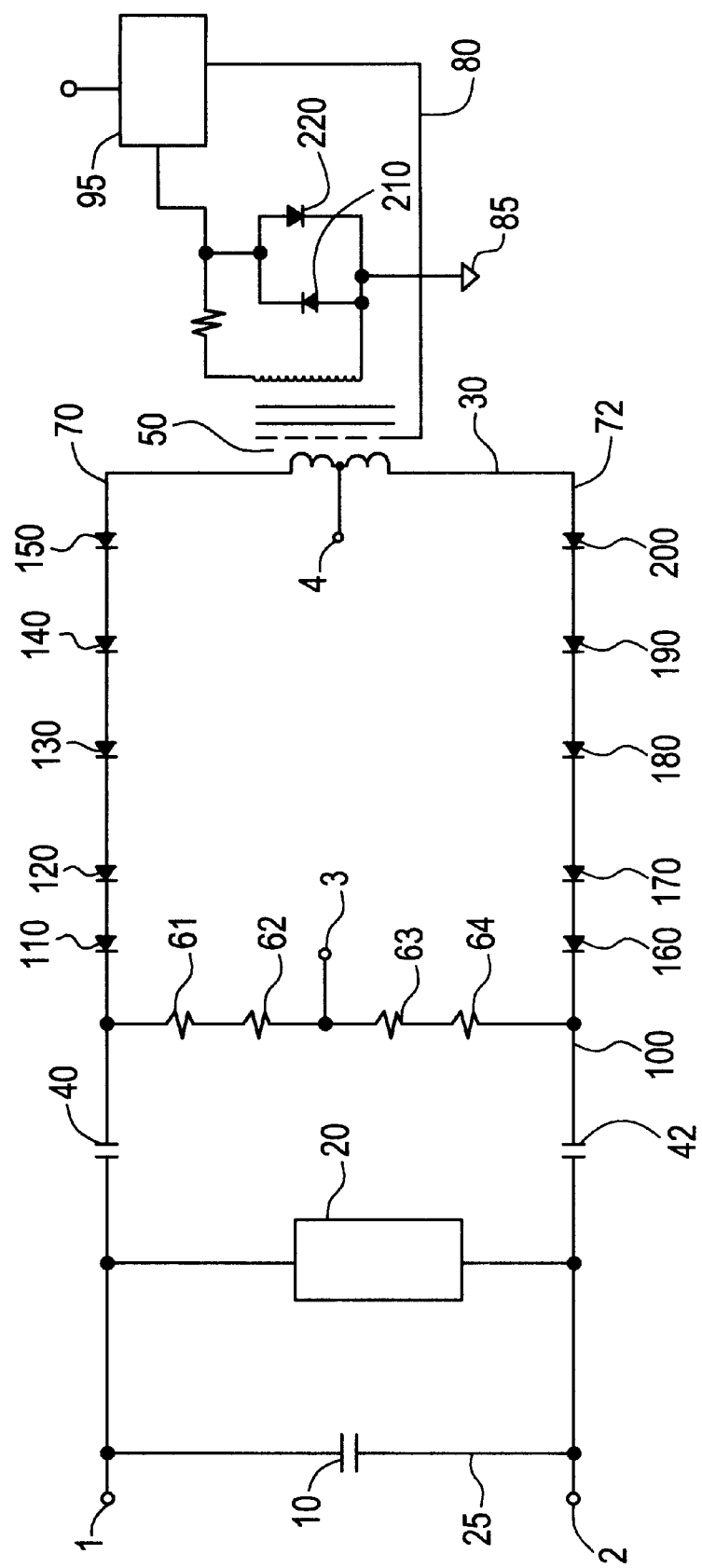
FIG. 3 is a schematic representation of an improved T/R switch for use with an EMAT, according to the preferred embodiment of the present invention.

Referring to the drawings generally, wherein like numerals designate the same or functionally similar elements throughout the several drawings, and to FIG. 3, in particular, there is shown a schematic diagram of the preferred embodiment of the invention. The T/R circuit 100 is a fast switching, balanced, transmitting and receiving switch with good common mode noise rejection for use with EMAT transducers. In operation, a large RF toneburst (100 to 500 volts peak) is applied at point 1 and point 2 in T/R circuit 100. Tuning capacitor 10 is used to resonate the inductance and resistance of EMAT coil 20 to the desired operating frequency. This tuned tank circuit 25, formed by EMAT coil 20 and tuning capacitor 10, is energized by an applied transmitter toneburst. Large RF currents flow in the tank circuit 25 and, therefore in EMAT coil 20. In turn, the RF current flow then launches ultrasonic signals in the workpiece in the presence of a magnetic field (not shown).

The T/R switching circuit 30 is formed by capacitor 40, capacitor 42, resistor 61, resistor 62, resistor 63, resistor 64, diode string 70, diode string 72, and transformer 50. Diode string 70 is formed by diode 110, diode 120, diode 130, diode 140, and diode 150. Diode string 72 is formed by diode 160, diode 170, diode 180, diode 190, and diode 200. Transformer 50 is preferably constructed with an electrostatic shield under the primary windings connected to the receiver ground, although the circuit can function adequately without such a shield. Input receiver circuit 80 includes diode 210, diode 220, and receiver input 95. The differential input receiver is also connected to transformer 50 and a grounded fixture 85. The T/R switching circuit 30 is balanced with respect to ground, providing high common mode noise rejection. Balancing with respect to ground is a well known method of preventing common mode noise on the primary windings from being capacitively coupled to the secondary windings.

A voltage source is applied to point 3 and point 4. Current flows through the center tapped primary winding on transformer 50. Since this current flows in opposite directions in the two halves of the center tapped primary winding, this DC current will not produce saturation of the core of transformer 50. The current then flows through diode string 70 on one side of the T/R switching circuit 30 and diode string 72 on the other side of the T/R switching circuit 30. However, this DC bias current is blocked by capacitor 40 and capacitor 42. Therefore, the current flows through resistor 61, resistor 62, resistor 63, and resistor 64, and then back to the power source. Capacitor 40 and capacitor 42 are chosen so that they are a very low impedance at the desired operating frequency.

During reception, a small signal induced on the EMAT coil 20 is coupled, via capacitor 40, capacitor 42, "on-biased" diode string 70, and "on-biased" diode string 72, to the primary winding of transformer 50. (Note: The transmitter output is in a high impedance state when not transmitting, thereby preventing the transmitter output from loading down the received signals.) Diode 210 and diode 220 are connected back to back across the input to the receiver circuit 80, thereby preventing large voltages from being generated at the input to input receiver 95 which might damage it.

During transmission, the large transmitter voltages applied to the T/R circuit 100 cause all the diodes in this circuit to be reverse-biased. A sinusoidal toneburst alternately reverse-biases diode string 70 and then diode string 72 as the voltage reverses polarity. Accordingly, all of the diodes then switch from conductive to nonconductive states within a few nanoseconds, as the applied voltage passes through zero and then reverse-biases diode string 70 and diode string 72. Consequently, all the diodes are switched into a nonconductive state, thereby preventing the large transmitter power from being applied to the primary windings of transformer 50. As soon as the transmitter voltage stops, the circuit is then ready to pass the smaller received signals to the receiver with very little attenuation.

The diodes employed in this circuit are very fast switching silicon diodes, although other types may also be used. These diodes switch in only a few nanoseconds, however their breakdown voltage is only about 100 volts each. Several diodes are used in the diode strings to increase the breakdown voltage to withstand the transmitter voltage when reverse biased.

While specific embodiments of the invention have been shown and described in detail to illustrate the specific application of the principles of the invention, it will be understood that the invention may be embodied as more fully described in the claims, or as otherwise understood by those skilled in the art, without departing from such principles.

We claim:

1. A transmitting and receiving switching circuit for an electromagnetic acoustic transducer (EMAT) comprising:

an EMAT coil;

a means for resonating the inductance and resistance of the EMAT coil at a desired frequency, connected to the EMAT coil;

a first means for selectively redirecting an electrical current, connected to the EMAT coil;

a second means for selectively redirecting the electrical current, connected to the first means for selectively redirecting the electrical current;

a means for resisting the electrical current, connected to the first means for selectively redirecting the electrical current and connected to the second means for selectively redirecting the electrical current;

a transformer, connected to the second means for selectively redirecting the electrical current;

an input receiver for detecting electrical signals, having an input port and connected to the transformer; and a voltage, selectively applied to the transformer and to the means for resisting the electrical current.

2. A switching circuit according to claim 1, wherein the first means for selectively redirecting the electrical current comprises a plurality of capacitors.

3. A switching circuit according to claim 1, wherein the second means for selectively redirecting the electrical current comprises a plurality of diodes.

4. A switching circuit according to claim 2, wherein the second means for selectively redirecting the electrical current is a plurality of diodes.

5. A switching circuit according to claim 3, wherein the diodes are fast switching silicon diodes.

6. A switching circuit according to claim 4, wherein the diodes are fast switching silicon diodes.

7. A switching circuit according to claim 1, wherein the means for resonating the inductance and resistance of the EMAT coil at a desired frequency comprises a tuning capacitor, connected to opposite ends of the EMAT coil, and the application of a controlled toneburst at opposite ends of the tuning capacitor.

8. A switching circuit according to claim 7, wherein the controlled toneburst has a voltage between 100 and 500 volts peak.

9. A switching circuit according to claim 1, wherein the input receiver further comprises a means for preventing large voltages from entering the input receiver.

10. A switching circuit according to claim 9, wherein the means for preventing large voltages from entering the input receiver comprises a plurality of diodes arranged in a back-to-back configuration across the input port to the input receiver.

11. A method for selectively switching an electromagnet acoustic transducer (EMAT) circuit, having a tuning capacitor, a plurality of capacitors, a plurality of diodes, a plurality of resistors, a transformer, and an input receiver, between transmitting mode and receiving mode comprising:

applying an initial toneburst across the tuning, capacitor and the EMAT coil;

resonating the inductance and resistance of the EMAT coil with the tuning capacitor to a desired frequency;

selectively applying a voltage across the transformer, the plurality of resistors, and the plurality of diodes whereby a transmission signal in the EMAT is produced;

selectively emitting a sinusodial toneburst across the plurality of diodes whereby the conductivity of the diodes is altered; and selectively monitoring the signal received by the input receiver whereby a receiving signal from the EMAT is detected.

12. A method according to claim 11, wherein the transformer includes a primary winding and wherein the voltage is applied to the transformer at the center of the primary winding of the transformer and to the mid-point of the plurality of resistors.

13. A method according to claim 11, wherein the initial toneburst is between a 100 and 500 volt peak.

* * * * *